Figure 1:
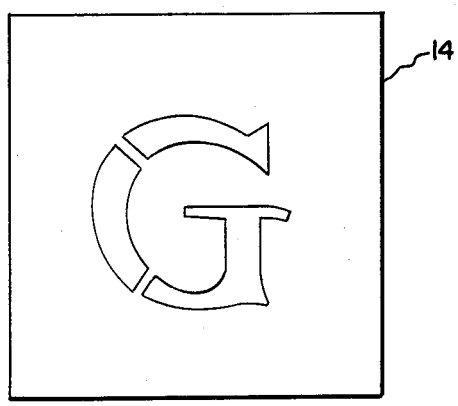

United States Patent [19]

Giaever et al.

[11] Patent Number: 4,672,024
[45] Date of Patent: Jun. 9, 1987

[54] IMMUNOLOGICAL DETECTION DEVICE AND METHOD FOR ITS PREPARATION

[75] Inventors: Ivar Giaever, Schenectady, N.Y.; Dale Harrigan, Tuskegee, Ala.

[73] Assignee: General Electric Company, Schenectady, N.Y.

[21] Appl. No.: 601,462

[22] Filed: Apr. 18, 1984

[51] Int. Cl.⁴ .......................... G03C 5/04; G01N 1/48; G01N 33/551; A61K 41/00

[52] U.S. Cl. ........................................ 430/396; 430/4; 422/56; 422/57; 436/524; 436/543; 436/810; 424/90; 427/2; 427/3; 427/54.1

[58] Field of Search ............... 436/524, 525, 527, 807, 436/810, 823, 824, 543; 422/56, 57; 424/90; 427/2, 3, 54.1; 430/4, 396

[56] References Cited

U.S. PATENT DOCUMENTS 3,914,408 10/1975 Mebus ................................... 424/89
4,011,308 3/1977 Giaever ............................... 424/1.5
4,018,886 4/1977 Giaver ................................. 424/12
4,216,245 8/1980 Johnson ............................... 422/56

OTHER PUBLICATIONS

"Protein Deposition on Field Emitter Tips and Its Removal by UV Radiation"-Panitz et al., [Surface Sci., 97, 25–42 (1980)].
Chemical Abstracts, vol. 91, No. 209056w, 1979.

Primary Examiner—Christine M. Nucker
Assistant Examiner—Patricia L. DeSantis
Attorney, Agent, or Firm—William A. Teoli; James C. Davis, Jr.; James Magee, Jr.

[57] ABSTRACT

An antigen-covered substrate is irradiated with ultraviolet light through a mask after which the exposed areas are rendered no longer antigenic. The unexposed areas retain their antigenic behavior and are available for the occurrence and detection of an immunological reaction.

3 Claims, 10 Drawing Figures

IMMUNOLOGICAL DETECTION DEVICE AND METHOD FOR ITS PREPARATION

BACKGROUND OF THE INVENTION

This invention relates to the detection of proteins by the utilization of the phenomenum by which such proteins interact specifically either immunologically or nonimmunologically.

Exemplary constructions of diagnostic devices for use in the immunological detection of proteins are disclosed in U.S. Pat. Nos. 3,926,564—Giaever, 4,011,308—Giaever, and 4,018,886—Giaever. An article "Protein Deposition on Field-Emitter Tips and Its Removal By UV Radiation" by Panitz and Giaever [Surface Sci. 97, 25–42 (1980)] describes the removal of protein from the surface of a metal-coated slide by the use of ultraviolet light in order to clean the surface.

The term "biological particle" is intended to encompass smaller proteins (e.g., plasma proteins, antigens, antibodies, lactins) and bodies of proteinaceous material (e.g., viruses, bacteria, cells) capable of stimulating antibody production, when injected into an animal and/or having the property of interacting specifically either immunologically or nonimmunologically.

Immunological reactions are highly specific biochemical reactions in which a first protein (e.g., an antigen) combines (links) with a second protein specific to the first protein (e.g., an antibody) to form an immunologically complexed protein. Immunological reactions taking place within a biological system, such as an animal or human being, are vital in combating disease. In a biological system, the entry of a foreign protein, i.e., an antigen, causes the biological system to produce the antibody proteins specific to the antigen by a process not fully understood at this time. The antibody protein molecules have available chemical combining or binding sites, which complement those of the antigen molecule, so that the antigen and antibody chemically link or bond to form an immunological complex protein.

Most antigens are proteins, or contain proteins as an essential part, whereas all antibodies are proteins. Proteins are large molecules of high molecular weight, i.e., they are polymers consisting of chains of various numbers of amino acids. A typical proteinaceous material will comprise multiple entities (e.g., protein molecules, cells, etc.), which do not adhere to each other. Therefore, when a proteinaceous material is brought into contact with a substrate, it deposites as a single layer. If the entities are molecular in size, this resulting single layer is monomolecular; if the entities are larger, the layer will be a thicker single layer. No other arbitrary protein will adhere to a deposited protein layer. On the other hand, specifically reacting protein to a protein adsorbed onto the substrate will immunologically bond thereto.

In accordance with the teachings in the above-cited patents, this phenomenum is exploited to provide medical diagnostic apparatus in which a substrate (e.g., a glass slide, the surface of which has been provided with a layer of metal, such as indium) having a first layer of one protein adsorbed thereon is used to test suspected solutions for the presence of the protein specific thereto (i.e. the protein specifically reacting therewith). If the specifically reacting protein is present in the solution, the substrate after exposure to the solution will have a double protein layer thereon. If the specifically reacting protein is absent from the solution, the slide after exposure to the solution will have only the original layer thereon. Optical, electrical, chemical and tagged-detection means for distinguishing between the presence of double and single protein layers are known in the art and in the aforementioned patents.

Because antibodies are produced by biological systems in response to invasions thereof by foreign proteins, the detection of antibodies in a biological system is of medical diagnostic value in determining the antigens to which the system has been exposed. A typical example of diagnostic detection of antibodies is the detection of antibodies to syphilis or gonorrhea in blood serum. Conversely, the detection of certain antigens in a biological system also has medical diagnostic value; examples of diagnostic detection of antigens include the detection of HCG protein molecules in urine as a test for pregnancy, and detection of hepatitis-associated-antigen (HAA) molecules in the blood of prospective blood donors.

In order to perform such diagnostic tests, the appropriate protein of the immunologically reacting pair must be obtained. The only known source of an antibody protein is a living biological system. More particularly, only vertebrates are known at this time to exhibit immunological reactions to the introduction of a foreign protein. For example, many antibodies are found in the blood serum of animals and human beings which have been exposed to the corresponding antigens. Many antigens, however, may be controllably produced in laboratory cultures. However, some antigens, for example, HAA molecules are at present like antibodies, only obtainable from the higher living biological systems.

It is known in the immunological art that antibody molecules function as antigens when introduced into the system of a vertebrate to whom they are foreign proteins. Accordingly, specifically reacting antibodies to a given antibody may readily be produced in such vertebrate system.

While emphasis herein for the purposes of exemplification will be on immunologically reactive biological particles (the simplest case being the antigen-antibody pair), it should be understood as explained at the onset that this invention is equally useful with sets of biological particles that undergo forms of biological interaction other than the immunologic reaction, the only criterion being that the particles must be mutually specific.

DESCRIPTION OF THE INVENTION

This invention is directed to a diagnostic device with improved readout for determining the presence or absence of select proteins in low concentration in a liquid sample and the method for its preparation. The device comprises in combination a layer of biological particles covering area of one major surface of a substrate, the surface preferably being metallic, with the biological particles disposed within at least one first part of the area having the capability for interacting with other biological particles specific thereto and at least one second part of the area in which the biological particles do not have the aforementioned capability. The second part immediately adjoins (i.e., borders upon) the first part in order to provide definition of the first part. Typically the first part of the overall area is shaped in a predetermined pattern to facilitate recognition of a positive test upon exposure to a liquid sample containing biological particles specific to those disposed within the first part of the area.

Figure 4:
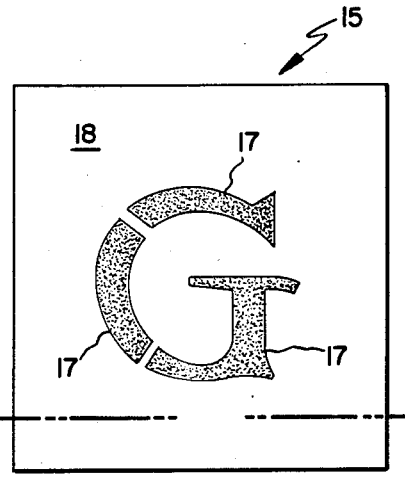
Figure 2:
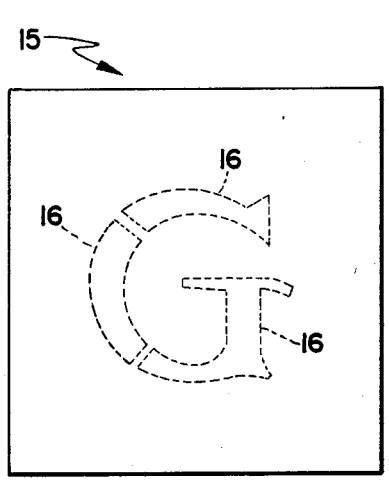
Figure 5:
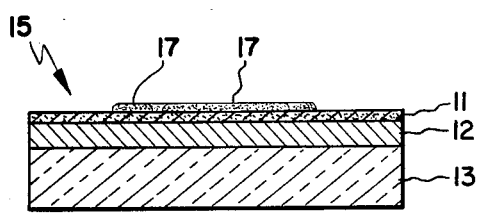
Figure 3:
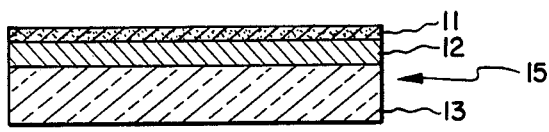
Figure 6:
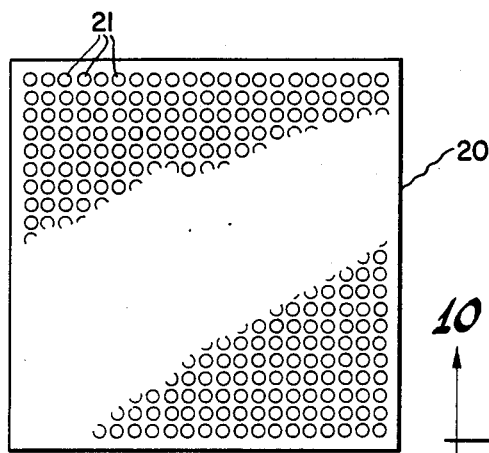
Figure 9:
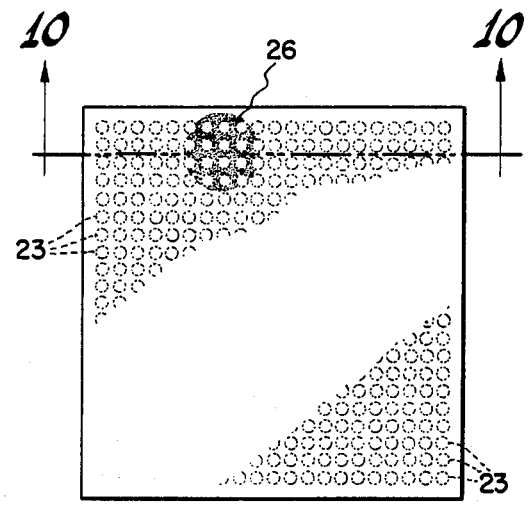
Figure 7:
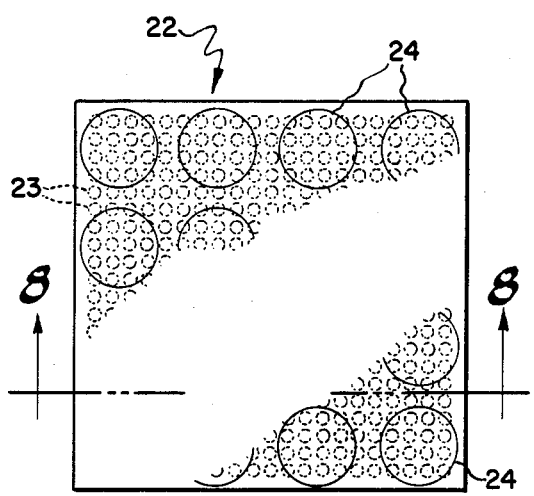
Figure 10:
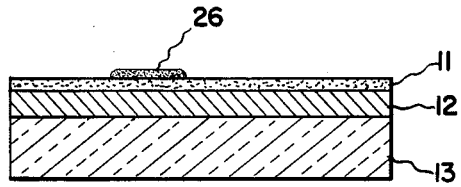
Figure 8:
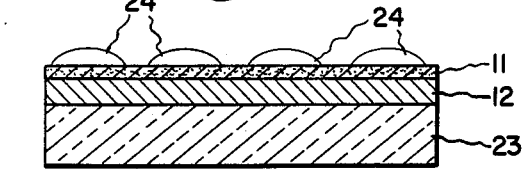

In the method for constructing a typical diagnostic device embodying this invention, a glass slide having a coating of indium metal on its surface is exposed to a solution containing antigen to cover the indium surface. After drying, this antigen layer is covered with a mask defining one or more predetermined patterns, e.g. as openings through the mask, and this assembly is exposed to ultraviolet light for a period of time sufficiently long to destroy the specificity of those biological particles exposed to the ultraviolet light through the mask. The exposure to ultraviolet light must be short enough (and the intensity of the source small enough) so that the protein layer remains intact.

Since most solids are opaque to ultraviolet light, the most feasible mask construction is a solid mask with openings therethrough, e.g. holes or cut-outs in special shapes. However, a mask can be made of material transparent to ultraviolet light such as quartz with opaque portions formed thereon.

By exposing the top surface of the diagnostic device to a solution containing antibodies specific to the antigen, the non-irradiated antigen pattern will pickup the specific antibody while the deactivated (radiated) antigen will not. This method of detection device preparation provides a convenient way to set down discrete patterns and permits the use of intricate patterns easily detectable by the unaided eye.

By having areas of irradiated biological particles bounded by the same biological particles that have been rendered inactive, detection of the specific reaction is enhanced, because of the increase in the optical density from its initial value, where the specific protein adheres over the predetermined pattern, which has retained its specificity. If the protein to be detected is absent from the serum, the predetermined patterns remain invisible because both the areas which have retained their specificity and those which have been rendered inactive have the same optical density.

This method has the special advantage that it lends itself to more accurate characterization of faint images that could be due to non-specific sticking of protein or to the presence of the select protein in very low concentration.

BRIEF DESCRIPTION OF THE DRAWING

The subject matter of the instant invention for which protection is sought is presented as claims at the conclusion of the written description of the invention set forth herein. The description sets forth the manner and process of making and using the invention and the accompanying drawing forms part of the description schematically illustrating one embodiment. The views include:

FIG. 1 is a plan view of an exemplary mask construction;

FIG. 2 is a plan view of a metallized glass plate coated with a protein layer that has been irradiated with ultraviolet light through the mask of FIG. 1 (mask removed);

FIG. 3 is a sectional view taken on line 3—3 of FIG. 2;

FIG. 4 is a plan view of the slide of FIG. 2 after exposure to biological particles specific to the active biological particles in the discrete patterned areas;

FIG. 5 is a sectional view taken on line 5—5 of FIG. 4.

FIG. 6 is a plan view of a second embodiment of mask construction;

FIG. 7 is a plan view similar to FIG. 2 of a protein-coated metallized glass irradiated using the mask of FIG. 6;

FIG. 8 is a sectional view taken on line 8—8 of FIG. 7;

FIG. 9 is a plan view of the slide of FIG. 7 after exposure to biological particles specific to the active biological particles in the area surrounding the discrete patterned areas, and FIG. 10 is a sectional view taken on line 10—10 of FIG. 9.

MANNER AND PROCESS OF MAKING AND USING THE INVENTION

As used herein, terms such as "metallized surface" or "surface being metallic" encompass both surface areas of metal and surface areas of metal containing the oxide of one or more metals present. The substrate used herein is preferably glass slide with a surface thereof metallized with indium. However, suitable substrates may also be prepared from metal, metallized plastic, or similar material although a method of readout other than the use of the unaided eye may be necessary.

Referring now to FIGS. 1 and 2 preparation of an exemplary diagnostic device according to this invention is as follows: A first layer 11 of immunologically reactive biological particles is deposited on the indium layer 12 adhered to glass slide 13. Coating 11 is usually applied by dipping the metal coated slide into a solution of the biological particles (e.g. some specific antigen). After drying the slide, the imposition of discrete patterns on the coated slide is accomplished by the use of mask 14 made of a material opaque to ultraviolet light having a cut-out replica of the desired pattern, in this case the letter "G".

With the mask 14 in place over the surface of layer 11, this layer is irradiated with ultraviolet light through the mask. The time of exposure is relatively short. In the case of an ultraviolet light source such Hanovia type SH high pressure mercury arc lamp, the exposure time would be about 3 minutes. The exposure period should be long enough to destroy the specificity of the biological particle(s) irradiated, but yet short enough so that the biological particles will not be removed from the surface by the exposure.

The exposed areas of coating 11 are eroded by the combined action of the ultraviolet radiation and ozone so that the pattern of keying sites on the biological particles that would be recognized by the select is are no longer present. The nature of this erosion mechanism is such that it is expected that in addition to applying to antigen-antibody couples and enzyme-substrate couples it should have general applicability to mutually specific biological particle couples.

After the irradiation step and subsequent removal of mask 14, the device 15 (as shown in FIG. 2) will have discrete patterned areas 16 occupied by non-irradiated biological particles and these patterns are surrounded by area in which the specificity of the protein layer has been destroyed. These patterns 16 cannot be seen by visual inspection (because there is no change in optical density) and are, therefore, shown in the drawings as regions defined by dotted lines. The device 15 is now ready for use.

Upon exposure of layer 11 to a sample of serum suspected of containing biological particles specific to those comprising patterned areas 16 one of two results will occur. If the specific biological particles are not present in the serum, spots 16 remain invisible, because no proteins will attach and no contrasting area(s) of optical density is produced. If the specific biological particles are present, they will become attached to by the biological particles in patterned areas 16 to form layers 17, but not by the surrounding previously irradiated area 18 as is shown in FIG. 4. The imposition of layers 17 over patterned areas 16 increases the optical density in these regions and patterned areas coincident with areas 16 now become visible to the naked eye.

Although a letter-shaped pattern has been described to illustrate the invention, more intricate patterns easily detectable by the eye may be created using an appropriate mask. The mask material may, of course, be transparent, rather than opaque, to ultraviolet light.

A second embodiment shown in FIGS. 6–10 is exemplary of a particularly effective mode of detecting the difference between a positive reading for a low concentration of the select protein and a negative reading caused by the spurious presence of non-specific protein.

Mask 20 of material opaque to ultraviolet radiation has a large number of very small holes (e.g. about 1 mm. in diameter) 21 in some preselected pattern, such as closely spaced rows extending at right angles to each other. After irradiation of a glass slide 22 (prepared as described for slide 15 hereinabove) through mask 20, layer 11 will be populated by a very large number of very small invisible irradiated areas 23. Only a portion of the irradiated areas are shown in the drawings to simplify the illustration.

This arrangement is of particular advantage in the screening of large numbers of samples to identify which one(s) contain the select protein. The screening is conveniently accomplished by applying a droplet 24 from each sample, each droplet covering several of the closely-spaced irradiated areas 23.

After an appropriate contact time, droplets 22 are washed off and slide 22 is examined. Any positive readout such as region 26 will consist of a layer of the select biological particles covering all of the area occupied by droplet 24 except for the irradiated areas 23. The readout is enhanced by the presence of several of the uncoated areas 23.

The embodiment of FIGS. 6–10 has been used to screen large numbers of samples of media from tissue cultures of hybridomas to determine which hybridomas (if any) is the one productive of the sought-for monoclonal antibodies. In one instance, the objective was to locate the medium containing monoclonal antibodies of aspartate aminotransferase. A slide 22 (covered with a layer of aspartate aminotransferase) was prepared with irradiated spots 23 in the form of 1 mm. diameter areas in rows 1 mm. apart. Droplets 24 (about 4 mm. in diameter) of media from candidate tissue cultures were applied, about 20 droplets per slide.

Still another useful configuration of irradiated/non-irradiated areas as part of a diagnostic device according to this invention is obtained by the use of a screen (e.g. of metal) as the mask, preferably a screen with very small (e.g. about 1 mm. square) openings.

What is claimed is:

1. A method for making a diagnostic device for detecting the presence or absence of select biological particles in a liquid sample comprising the steps of
   (1) contacting the surface of a substrate with a layer of antigen particles specific for the detection of the select biological particles,
   (2) contacting the antigen coated substrate surface with a patterned mask,
   (3) irradiating the patterned mask-treated substrate composite with UV light for a period of time sufficient to destroy the specificity of irradiated antigen particles for the select biological particles, and
   (4) removing the mask.
2. A diagnostic device made in accordance with the method of claim 1.
3. The device of claim 2 where the substrate is an indium substrate.

* * * * *